(12) United States Patent
Howanec, Jr. et al.

(10) Patent No.: US 6,503,274 B1
(45) Date of Patent: Jan. 7, 2003

(54) METHOD OF IMPLANTING A FLEXIBLE ANNULOPLASTY SYSTEM

(75) Inventors: Myron Howanec, Jr., Corona, CA (US); Michael John Scott, Lake Forest, CA (US); Brian Eugene Brutcher, Santa Ana, CA (US); Jerry L. Jackman, Tustin, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 32 days.

(21) Appl. No.: 09/708,895

(22) Filed: Nov. 8, 2000

Related U.S. Application Data

(62) Division of application No. 09/293,214, filed on Apr. 16, 1999, now Pat. No. 6,183,512.

(51) Int. Cl.$^7$ .................................... A61F 2/06

(52) U.S. Cl. ...................... 623/2.37; 623/904

(58) Field of Search ............... 623/2.36, 2.42, 623/2.37, 904; 128/898

(56) References Cited

U.S. PATENT DOCUMENTS

| | | | |
|---|---|---|---|
| 4,204,542 A | 5/1980 | Bokros et al. | |
| 4,217,665 A | 8/1980 | Bex et al. | |
| 4,261,342 A | 4/1981 | Aranguren Duo | |
| 4,372,293 A | * | 2/1983 | Vijil-Rosales ............... 128/898 |
| 4,452,235 A | 6/1984 | Reyonlds | |
| 4,489,446 A | 12/1984 | Reed | |
| 4,792,336 A | 12/1988 | Hlavacek et al. | |
| 5,064,431 A | 11/1991 | Gilbertson et al. | |
| 5,300,116 A | 4/1994 | Chirila et al. | |
| 5,306,296 A | 4/1994 | Wright et al. | |

(List continued on next page.)

FOREIGN PATENT DOCUMENTS

| | | |
|---|---|---|
| EP | 0495417 A1 | 7/1992 |
| SU | 1127574 A | 12/1984 |
| SU | 1335260 A1 | 9/1987 |
| WO | WO 91/17721 | 11/1991 |
| WO | WO 93/15690 | 8/1993 |
| WO | WO 95/03755 | 2/1995 |
| WO | WO 95/16407 | 6/1995 |
| WO | WO 97/16135 | 5/1997 |
| WO | WO 97/19655 | 6/1997 |
| WO | WO 98/32401 | 7/1998 |

OTHER PUBLICATIONS

The Journal of Thoracic and Cardiovascular Surgery, vol. 110, No. 5.*
The Annals of Thoracic Surgery, vol. 46, No. 3 Sep. 1988.*
Hecart, et al.; *Technique for Tricuspid Annuloplasty With a Flexible Linear Reducer*, J Thorac Cardiovascular Surg., 79:689–692, 1980.
Abstract—*Surgical Treatment of Mitral Insufficiency Using Annuloplasty Suture Technic*, Orv Hetil 1999 Feb. 7.
Abstract—*Treatment of Functional Tricuspid Insufficiency by a Valvuloplasty With a Flexible Linear Reducer*, Arch Mal Coeur Vaiss 1979 Mar.

Primary Examiner—David H. Willse
Assistant Examiner—Suzette J. Jackson
(74) Attorney, Agent, or Firm—Debra D. Condino; John Christopher James; Guy L. Cumberbatch

(57) ABSTRACT

A design and method of implantation is disclosed for a flexible annuloplasty system for repairing a valve in a patient's heart. The annuloplasty system includes an elongate, flexible band with a needle attached to one end of the band and a fit adjuster attached to the other end of the band. The band is made of silicone and includes a plurality of fibers that are configured to prevent axial elongation of the band. In addition, the plurality of fibers ensure that a suture will catch on the fibers and prevent the suture from tearing out of the band.

31 Claims, 12 Drawing Sheets

U.S. PATENT DOCUMENTS

| | | | |
|---|---|---|---|
| 5,450,860 A | * | 9/1995 | O'Connor .................... 606/61 |
| 5,607,471 A | | 3/1997 | Seguin et al. |
| 5,674,279 A | | 10/1997 | Wright et al. |
| 5,674,280 A | | 10/1997 | Davidson et al. |
| 5,716,397 A | | 2/1998 | Myers |
| 5,776,189 A | | 7/1998 | Khalid |
| 5,824,066 A | | 10/1998 | Gross |
| 6,159,240 A | * | 12/2000 | Sparer et al. .............. 623/2.36 |
| 6,183,512 B1 | * | 2/2001 | Howanec, Jr. et al. ..... 623/2.36 |
| 6,250,308 B1 | * | 6/2001 | Cox ........................... 128/898 |

* cited by examiner

METHOD OF IMPLANTING A FLEXIBLE ANNULOPLASTY SYSTEM

RELATED APPLICATION

The present application is a divisional of application Ser. No. 09/293,214, filed Apr. 16, 1999 now U.S. Pat. No. 6,183,512.

FIELD OF THE INVENTION

The present invention relates to an annuloplasty system and methods for using such system during surgical procedures. The present invention particularly relates to annuloplasty bands and methods of using such bands in the repair of weakened or diseased heart valves.

BACKGROUND OF THE INVENTION

The correction of heart valve defects, such as valvular insufficiency, may be accomplished through various surgical interventions, including surgical replacement of the entire valve, repairing the valve leaflets, shortening or replacing the chordae tendinae or repairing the valve annulus. Although prosthetic devices are often used to replace dysfunctional or diseased valves, this approach is quite traumatic to the patient and requires lengthy and difficult surgical procedures. Hence, the preferred method of treating such valves is to perform, if possible, more conservative surgical procedures that address the problem yet preserve the patient's native valve.

A variety of such procedures have been developed to correct heart valve defects without resorting to a full valve replacement. An example of such a procedure is that which was developed by Dr. Norberto G. De Vega in the early 1970s. Dr. De Vega's procedure involves creating one or more seams within the tissue along the periphery of a weakened section of heart valve using conventional suture material. The suture is laced through the tissue along the periphery of the valve and the ends of the suture are pulled together in a "purse string" manner to constrict the annulus of the valve so that the valve is patent. The ends of the suture are then tied in place to retain the tissue in a plicated orientation.

Dr. De Vega's procedure offered many advantages for the cardiac surgeon and the patient. In particular, the procedure is sufficiently safe since it introduces a limited amount of foreign material with blood exposure within the heart thereby reducing the risk of thrombosis and is relatively effective at correcting valvular insufficiency. In addition, the procedure required little specialized equipment and could be rapidly performed with minimal training.

However, there were also serious drawbacks associated with Dr. De Vega's technique. For example, there have been several instances whereby the suture that is laced through the tissue along the periphery of the valve pulls out of the tissue. As a result, the suture tends to "guitar string" across the valve annulus forming an obstruction across the valve opening. Another problem is the bunching of tissue around the periphery of the valve caused by the "purse string" design. The bunched tissue causes the valve opening to distort from its natural shape thereby impeding proper valve function.

Another procedure was developed that addressed many of the problems associated with Dr. De Vega's technique. Dr. Alain Carpentier designed a series of multi-sized fabric covered rings with a stainless steel or titanium core. The rings are configured to approximate the original shape of the diseased or dysfunctional valve annulus. Dr. Carpentier's procedure involves sizing the annulus of the valve using a sizing template and selecting a corresponding fabric covered ring. A number of sutures are sewn around the periphery of the annulus creating a circle of guide lines. The ring is positioned on the valve annulus and the guide lines are then attached to the ring, thereby drawing the valve opening to the configuration of the ring and the approximate shape of the original valve annulus. Although Dr. Carpentier's method significantly improves valve function, some surgeons believe that the rigid rings somewhat compromise the natural flexibility of the valve due to the ring's rigid structure.

In response, rings having greater flexibility have also been introduced. Such flexible rings avoid constraining the natural flexibility of the annulus, yet still assist greatly in improving valve function. There are some disadvantages with flexible rings as well. For example, when the suture spacing on the annulus is not matched to the spacing on the ring, tension may result in the tissue and the device, further causing puckering in the tissue. Another example involves the loss of annulus flexibility over time. Since the flexible ring is secured to the valve annulus with a large number of sutures, scarring and stiffening of the valve annulus may develop. This results in a valve physiology similar to what may result when a rigid ring is installed, whereby the natural flexibility of the valve may be somewhat compromised.

A more recent flexible ring design has been proposed in U.S. Pat. No. 5,450,860 to address some of the aforesaid drawbacks. The flexible ring design in this patent includes an open ring in the form of a wide, flexible ligament that is implanted into the valve annulus. The ligament is typically made of expanded polytetrafluoroethylene to give the ligament its flexibility, promote tissue ingrowth and allow sutures to readily pass through it. Although this design substantially removes the ring from the blood flow in the valve, it has some inherent shortcomings.

For example, the material characteristics of the ligament have a tendency to cause the ligament to elongate or stretch when subjected to loading during implantation of the device in the annulus and once the heart is re-started. As a result, the valve structure and function may be compromised. In addition, this ligament design does not ensure the prevention of sutures tearing through the material when the ligament is anchored to the tissue. Therefore, there is a potential risk that the sutures will tear through the ligament, either during the implantation procedure or after the ligament has been implanted in the valve annulus, thereby resulting in valve insufficiency.

In view of the foregoing, it is apparent that a number of surgical procedures have been developed that avoid the dramatic step of replacing a native heart valve yet still assist in restoring normal valve function. It is also apparent, however, that these more conservative procedures still require improvement, particularly as it relates to the drawbacks associated with use of a flexible annuloplasty device. In particular, it is apparent that there is a continuing need to provide an annuloplasty system with a more durable prosthesis that minimizes blood exposure and is also safe and effective to use. There is also a need to provide a method of implanting such an improved prosthesis that requires a limited amount of specialized equipment, has a fast learning curve and can be performed in a minimal amount of time.

OBJECTS AND SUMMARY OF THE INVENTION

In view of the foregoing, it is an object of the present invention to provide an annuloplasty system that addresses the obstacles and disadvantages associated with prior annuloplasty prostheses and procedures.

A further object of the present invention is to provide an annuloplasty system that introduces a limited amount of foreign material to blood exposure within the heart thus reducing the risk of thrombosis.

A further object of the present invention is to provide an annuloplasty system that safely and effectively corrects valvular insufficiency.

A further object of the present invention is to provide an annuloplasty system that requires a limited amount of specialized equipment for installation, has a fast learning curve and can be performed in a minimal amount of time.

A further object of the present invention is to provide an annuloplasty system that provides sufficient structural support to the annulus yet maintains the valve's optimal functional shape and natural flexibility.

A further object of the present invention is to provide an annuloplasty system that maintains its flexibility over time.

A further object of the present invention is to provide an annuloplasty system that minimizes the potential of a suture tearing out of the device and tissue of a patient.

A further object of the present invention is to provide an annuloplasty system that includes a fit adjuster that is used to size and position the device in the annulus.

These and other objects not specifically enumerated herein are believed to be addressed by the present invention which contemplates an annuloplasty system for repairing a valve in a patient's heart comprising a needle, a band and at least one reinforcing filament. The needle and band each have a distal end and a proximal end. The proximal end of the band is attached to the distal end of the needle. In addition, the reinforcing filament extends along a length of the band.

The present invention also contemplates a method of implanting an annuloplasty device in a patient's heart to correct valvular insufficiency. The method may include the steps of providing an annuloplasty band having at least one fiber along its length and a needle attached to one end of the band and inserting the needle into the endocardium adjacent to a first trigone of a valve annulus. Further steps may include maneuvering the needle and band through the tissue of the arterioventricular (AV) groove of the annulus and directing the needle to exit the tissue adjacent to a second trigone of the valve annulus. The final step would likely include securing the band to the valve annulus using a suture that penetrates through the band.

BRIEF DESCRIPTION OF THE DRAWINGS

Other features and advantages of the present invention will be seen as the following description of particular embodiments progresses in conjunction with the drawings, in which.

DETAILED DESCRIPTION OF THE INVENTION

Figure 1:
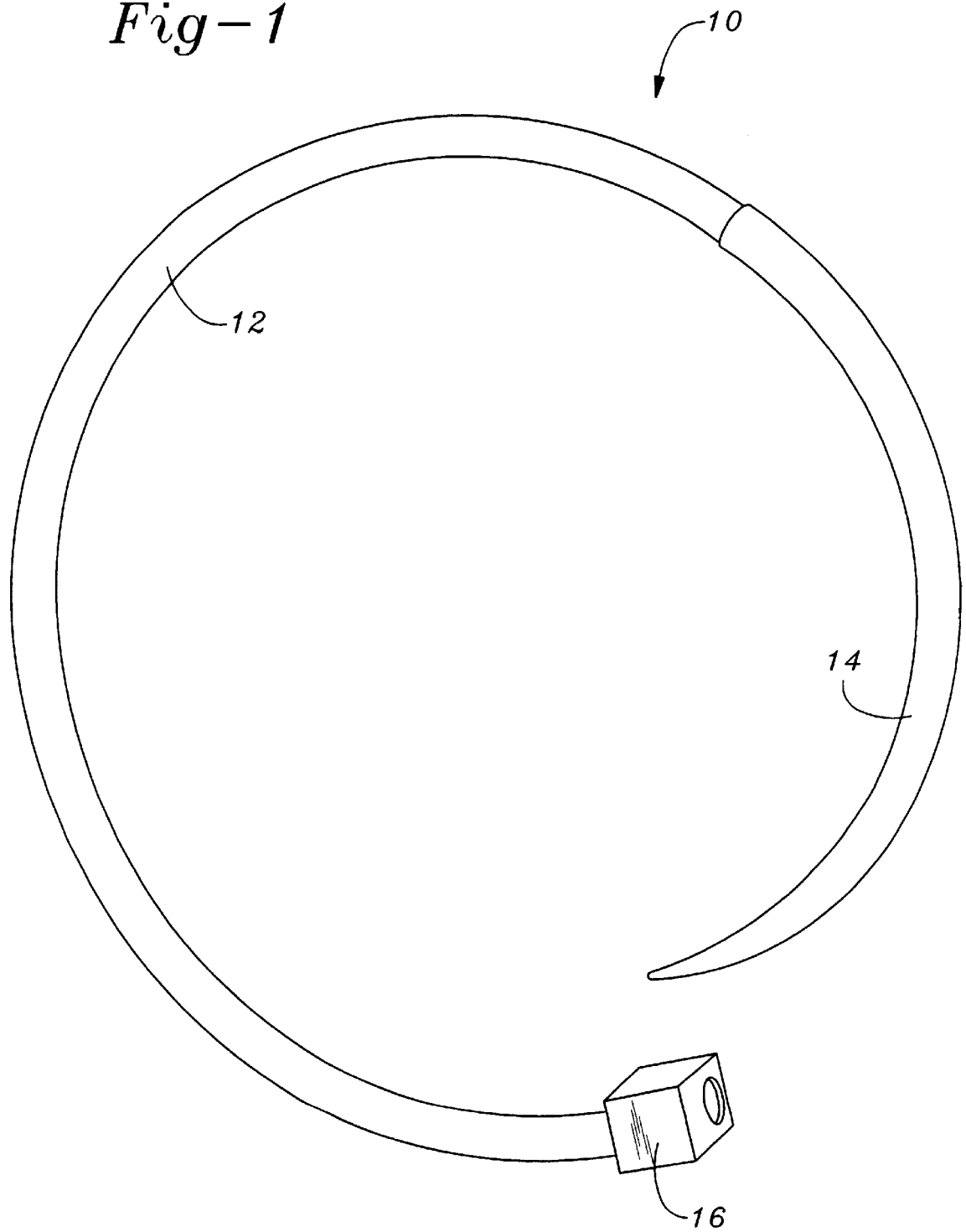
FIG. 1 is a perspective view of a non-distensible, flexible annuloplasty system in accordarice with the present invention.

Referring to FIG. 1, an embodiment of a non-distensible, flexible annuloplasty system 10 used to support a weakened and/or repaired heart valve in accordance with the present invention includes a non-distensible, elongate flexible band 12 with a needle 14 attached to one end of the band 12 and a fit adjuster 16 attached to the other end of the band 12. The band 12 typically has a round or elliptical cross-section and is solid throughout its length. In its relaxed state, the configuration of the band 12 is relatively straight. However, the flexibility of the band 12 allows it to be configured to the shape of the valve annulus with minimal elongation along its axis due to the band's 12 material characteristics and structure.

The band 12 must be long enough to extend along the fatty-tissue perimeter of the annulus of the valve (not shown) from one trigone, or commissure, to the other trigone and to allow for easy implantation by an appropriately skilled surgeon. This area where the band is implanted is commonly referred to as the AV groove. The AV groove is in the same plane of the valve annulus and contains a fatty pad. The length of the band 12 is preferably 38.0 cm, but can be as small as 2.54 cm based upon the size of the patient's annulus. Optimally, the length of the band 12 is 31.0 cm or more.

In a preferred embodiment, the overall diameter of the band 12 is 2.0 mm. However, the diameter of the band 12 can be at least 0.5 mm and still provide sufficient size to permit a conventional suture to be securely threaded through the band 12 or other surgical attachment device to secure the band to the patient's annulus.

Figure 2A:
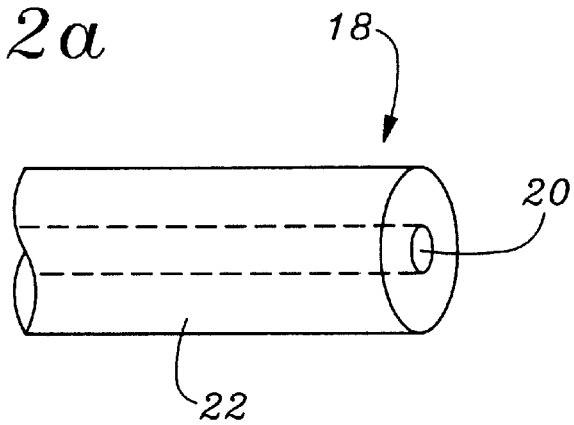
FIG. 2a is a cross-sectional perspective view of an annuloplasty band in accordance with a preferred embodiment of the present invention.
Figure 2B:
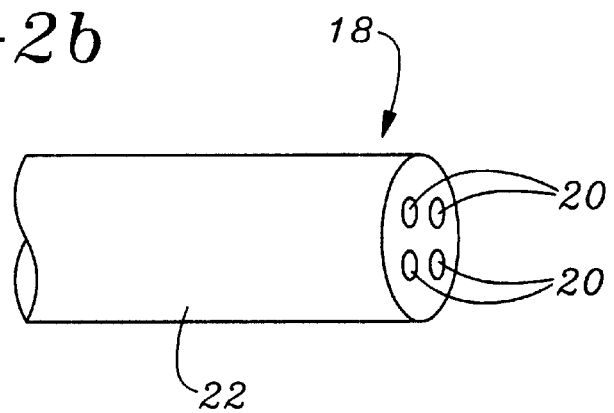
FIG. 2b is a perspective view of an annuloplasty band in accordance with a preferred embodiment of the present invention.

As shown in FIG. 2a, in one embodiment, the central core 18 of the band 12 includes one reinforcing filament 20 that extends along the length of the band 12 and a matrix element 22 surrounds the reinforcing filament 20. The diameter of the central core 18 is typically within the range of 0.5 to 1.0 mm. Another embodiment, shown in FIG. 2b, the central core 18 includes four reinforcing filaments 20 that are located within the central core 18. The number of reinforcing filaments 20 located in the central core 18 is determined by the strength of the material. For example, if a 4.0 suture is used for the reinforcing filament 20, then typically a quantity of 4 reinforcing filaments 20 would be located within the central core 18 to provide sufficient strength to the band 12.

Figure 2C:
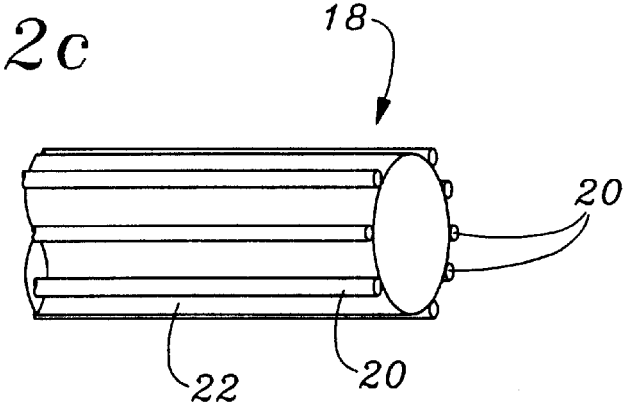
FIG. 2c is a perspective view of another embodiment of an annuloplasty band in accordance with a preferred embodiment of the present invention.

Another embodiment, shown in FIG. 2c, a plurality of reinforcing filaments 20 are located on the outside surface of the central core 18. In the alternative, in certain circumstances, it may be acceptable to have only one reinforcing filament 20 on the outside surface. Since the main functions of the reinforcing filament 20 are to provide structural strength and resist elongation or extension of the band 12, the reinforcing filament 20 can be located anywhere within or on the band 12.

The reinforcing filament 20 is made of long-term implant compatible material such as polyester, polytetrafluoroethylene (PTFE), polypropylene, silk, nylon and other non-resorbable materials. Preferably, the reinforcing filament 20 is made of a polyester suture. The reinforcing filament 20 can be comprised of fiber, thread, braid, suture, cloth or knit. Thus, the reinforcing filament 20 can practically be made of any monofilament or multifilament material or textile that can be implanted for long period of time within a patient.

In addition to the reinforcing filament 20, the central core 18 also includes a matrix element 22. The matrix element 22 is preferably made from silicone, however other materials such as PTFE, expanded polytetrafluoroethylene (ePTFE), polyurethane and the like can also be used. Silicone, however, is the preferred material since it allows easy insertion of, for example, an implant needle suture due to its lubricity and provides sufficient flexibility to the band 12. In addition, silicone has been extensively used in a variety of medical applications and, therefore, is clinically proven to be highly biocompatible.

The matrix element 22 must be of sufficient thickness to prevent the reinforcing filaments 20 from expanding or contracting after the matrix element 22 has been applied. In addition, the matrix element 22 creates a structure that binds (in the case of embodiments such as FIGS. 2b and 2c) the reinforcing filaments 20 together, thereby maintaining their configuration. The matrix element 22 can be applied to the reinforcing filaments 20 through various manufacturing methods that are well known in the art. For example, with tension placed along the axis of the reinforcing filaments 20, the matrix element 22 can be coated onto the reinforcing filaments 20 using an extrusion process. As alternative examples, the matrix element 22 can also be sprayed, dipped, molded or the like onto the reinforcing filaments 20.

Figure 3A:
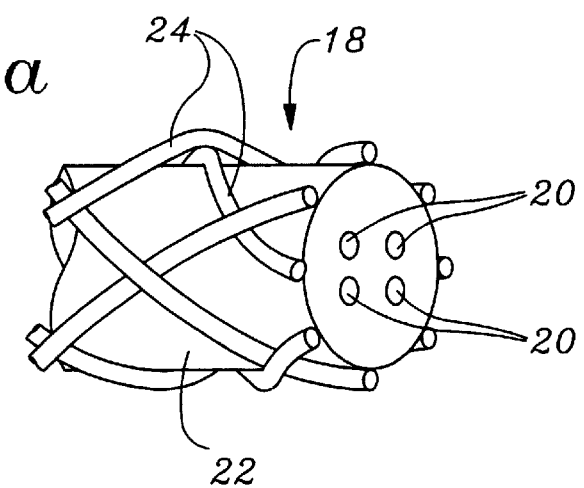
FIG. 3a is a perspective view of an embodiment of an annuloplasty band in accordance with a preferred embodiment of the present invention.
Figure 3B:
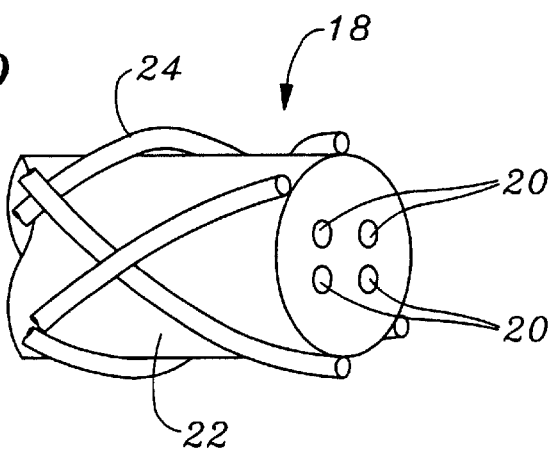
FIG. 3b is a perspective view of another embodiment of an annuloplasty band in accordance with a preferred embodiment of the present invention.
Figure 3C:
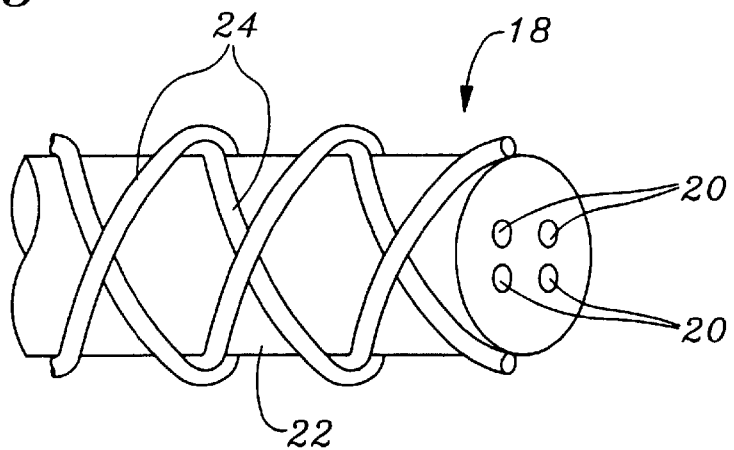
FIG. 3c is a perspective view of another embodiment of an annuloplasty band in accordance with a preferred embodiment of the present invention.

As shown in additional embodiments in FIGS. 3a–3c, an overwrap layer 24 surrounds the central core 18. The overwrap layer 24 is comprised of a plurality of fibers that are configured in an interlaced manner to ensure that a suture, or other surgical attachment device, placed through the band by a surgeon will catch on the fibers and prevent the suture from tearing out of the band 12 when the band 12 is secured to tissue during implantation. The plurality of fibers can include various configurations such as braid, weave, knit, helical wrap or other similar arrangements and is made of materials similar to those used for the reinforcing filament 20.

Figure 4:
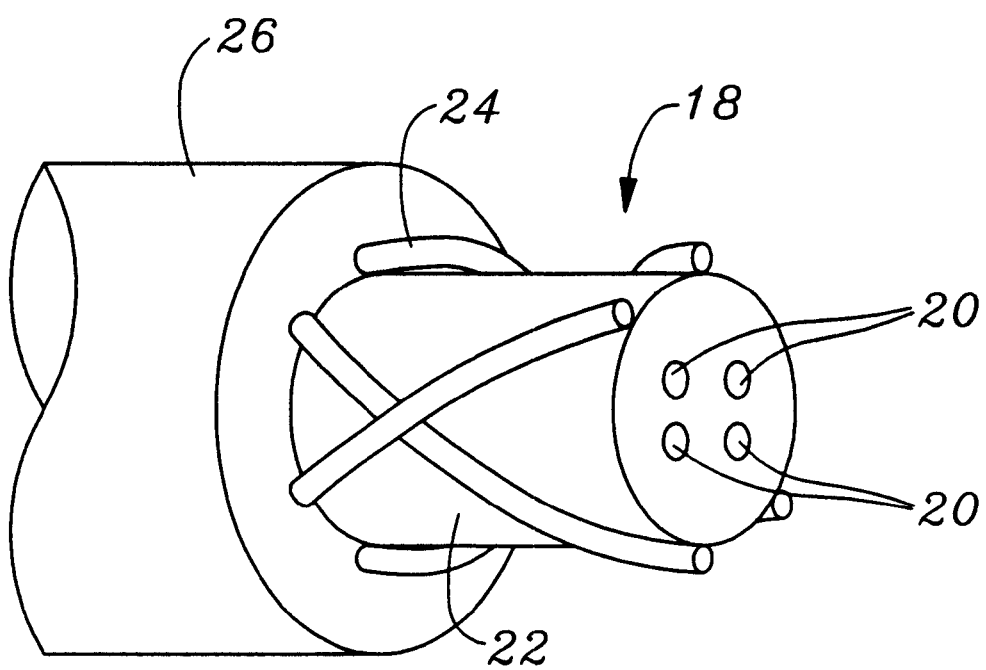
FIG. 4 is a perspective view of a band including an annuloplasty band in accordance with a preferred embodiment of the present invention.

A final overcoat layer 26 surrounds the overwrap layer 24 of the central core 18, as shown in a further embodiment of FIG. 4. The overcoat layer 26 is preferably made of silicone, however other comparable materials such as PTFE, ePTFE and polyurethane can also be used. Silicone is the preferred material since it discourages tissue ingrowth and provides sufficient flexibility to the band 12. In addition, the overcoat layer 26 is of minimal thickness, so that the fibers are closer to the surface of the band 12 to ensure capture by a suture, yet still provides a smooth, lubricious outer surface that allows the band 12 to easily slide through tissue.

The overcoat layer 26 can be applied onto the overwrap layer 24 using manufacturing methods similar to those previously described for the matrix element 22. The overcoat layer 26 should be sufficiently thick to adequately coat or surround the overwrap layer 24 so as to secure the overwrap layer 24 to the central core 18 and allow the band 12 to readily pass through tissue.

To verify that the band 12 is functioning properly in the valve annulus of a patient after implantation, it is advantageous for the band 12 to contain a component that can be easily detected using conventional detection methods. In one embodiment, the matrix element 22 and/or overcoat layer 26 contain a component that attenuates x-ray radiation to a greater degree than tissue. The component can be Barium, Bismuth or other similar components, and in a preferred embodiment the component is Barium Sulfate Thus, when a patient is imaged with x-ray energy, the radiation beam passes through the bone and soft tissue of the patient and is scattered by the band 12. The resultant image shows the location and configuration of the band 12 surrounding the annulus. Other non-invasive diagnostic imaging methods, such as ultrasound, computed tomography, magnetic resonance and the like, and their corresponding material components can also be used to image the device after implantation.

Figure 5:
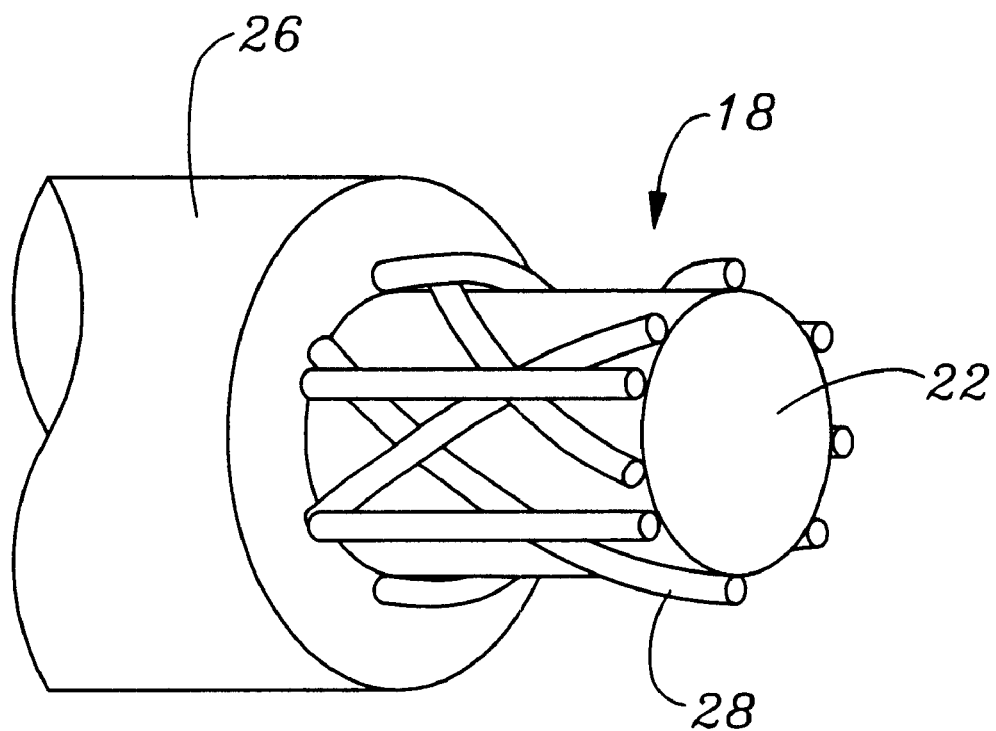
FIG. 5 is a perspective view of another embodiment of an annuloplasty band in accordance with a preferred embodiment of the present invention.

In another embodiment of the present invention, the reinforcing filament 20 and overwrap layer 24 are replaced by a single layer of a tubular woven, knit, braided or other textile 28, as shown in FIG. 5. The tubular textile 28 provides the same material characteristics that the combination of the reinforcing filament 20 and overwrap layer 24 provide. In this embodiment, the silicone layers may be simultaneously extruded inside and outside of the tubular textile 28. The main benefit of this particular configuration of the band 12 is ease of manufacturability. The fit, form and function of this embodiment is essentially the same as that of the previously described embodiment of the band 12.

Figure 6A:
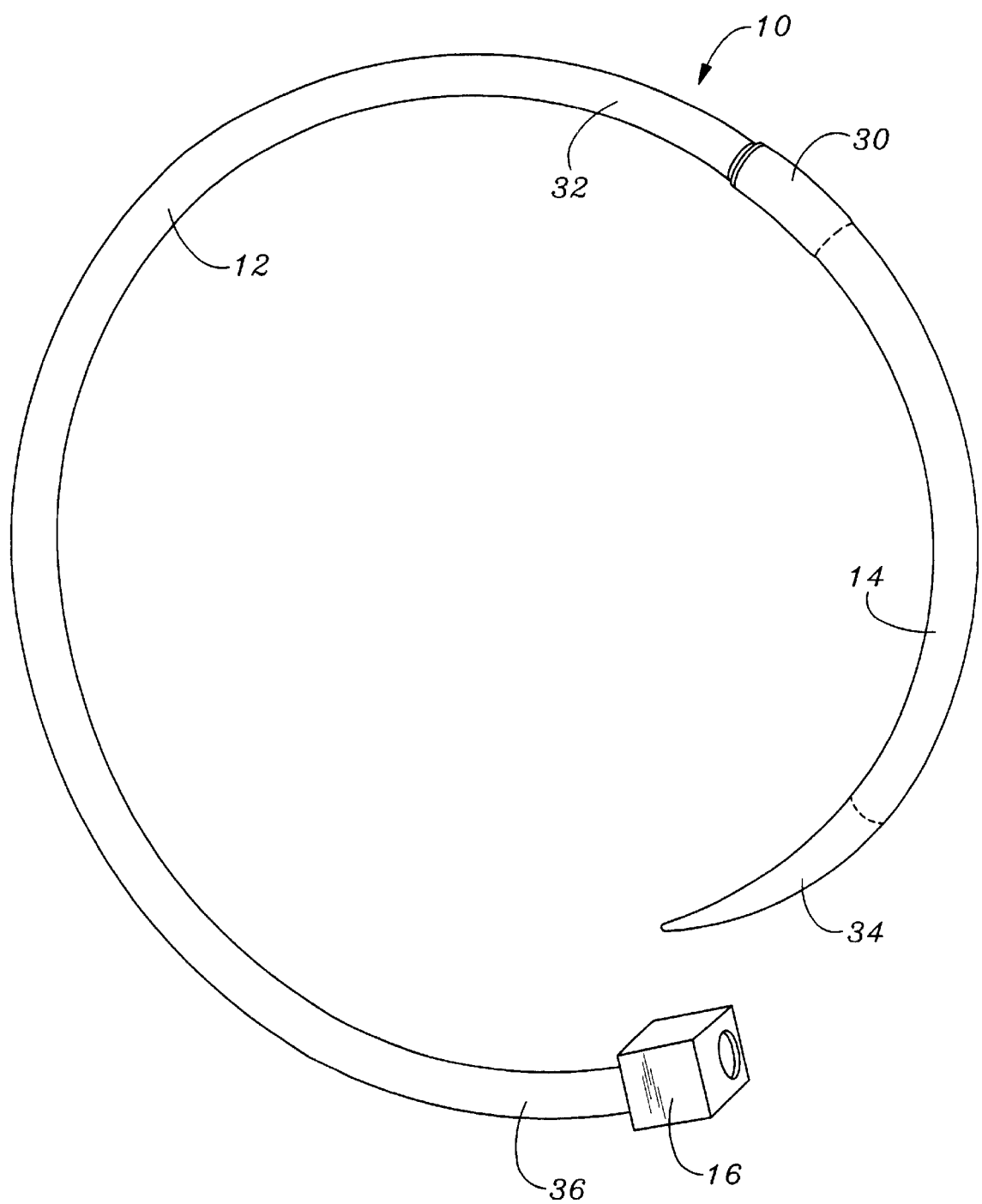
FIG. 6a is a perspective view of a non-distensible flexible annuloplasty system in accordance with a preferred embodiment of the present invention.

Referring to FIG. 6a, the annuloplasty system 10 of the present invention includes an arc-shaped needle 14 having its distal end 30 attached to the proximal end 32 of the band 12 and its proximal end 34 formed in the shape of a taper. The needle 14 is made of a single piece of material with an overall length in the range of 1.0 to 5.0 cm. In use, the preferred needle 14 length is based upon the size and shape of the patient's valve annulus. The needle 14 is typically made of stainless steel, however other medical-grade alloys or polymers that are highly corrosion resistant and approved for tissue contact can also be used. In addition, the material must be of sufficient strength and stiffness to allow the needle 14 to penetrate the tough, fibrous tissue of the endocardium and the AV groove.

The radius of the arc-shaped needle 14 is in the range of 10 to 50 mm, and is preferably sized to fit the valve annulus. In order to penetrate and maneuver through the tissue of the annulus, the proximal end 34 of the needle 14 forms a taper that is sharp enough to penetrate the tissue, yet sufficiently blunt to prevent unintentional damage to surrounding tissue and to remain in the AV groove during needle 14 insertion. Preferably, the preferred radius of the tip of the tapered portion of the needle 14 is about 0.762 mm, but can be within the range of approximately 0.127 mm to 2.032 mm.

The distal end 30 of the needle 14 is securely attached to the proximal end 32 of the band 12 to prevent detachment during the surgical procedure. The method of attaching the band 12 to the needle 14 may include mechanical or chemical means. For example, in one embodiment, the distal end 30 of the needle 14 includes a hollowed-out portion that is of sufficient size to allow insertion of the proximal end 32 of the band 12. Upon insertion, the hollow portion of the needle 14 is mechanically crimped thereby securing the band 12 to the needle 14.

In an alternate embodiment, an adhesive, such as medical grade cyanoacrylate or other similar adhesives, is used to bond the band 12 to the needle 14. Although the adhesive may be used alone or in combination with the mechanical crimping of the end 30 of the needle 14, the preferred embodiment is to use the combination of adhesive and mechanical crimping.

Figure 6B:
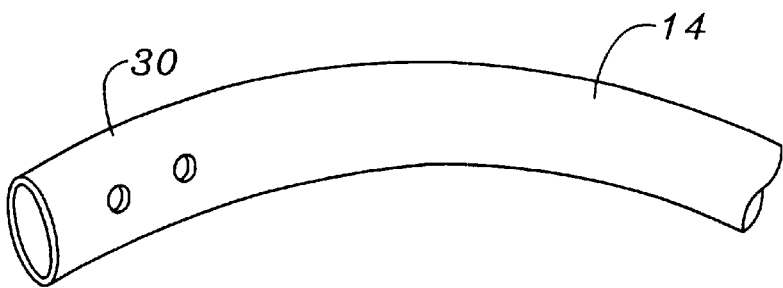
FIGS. 6b–6f are perspective views of various embodiments of attaching a band to a needle in accordance with a preferred embodiment of the present invention.

In another embodiment, shown in FIG. 6b, the hollowed-out portion of the needle 14 includes one or more through-holes. After the band 12 is inserted into the hollowed-out portion of the needle 14, the needle 14 is sutured onto the band 12 via the through-holes.

Figure 6C:
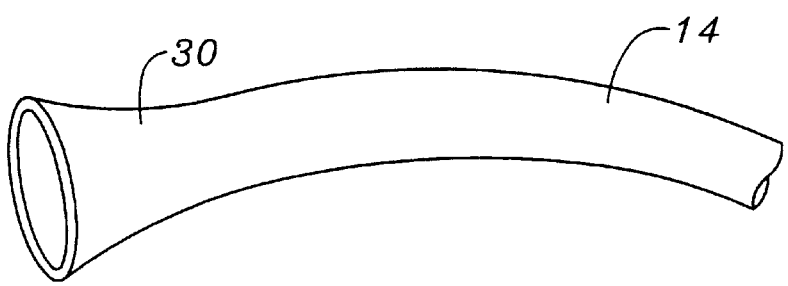
Figure 6D:
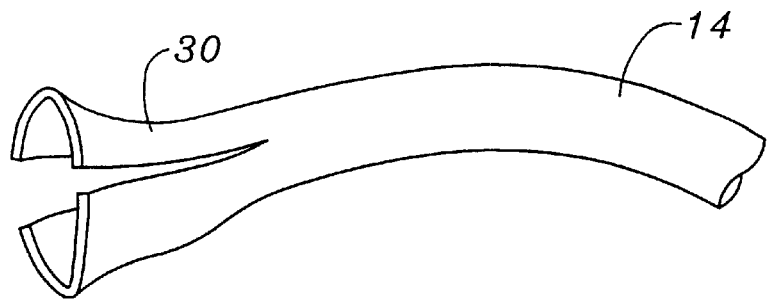

In yet another embodiment, the hollow portion of the needle 14 is flared in a radially-outward direction, as shown in FIG. 6c. The flared portion may be a continuous-flare or sectioned-flare. The sectioned-flare, shown in FIG. 6d, consists of one or more longitudinal cuts along the axis of the hollow portion of the needle 14. Upon insertion of the end 32 of the band 12 into the flared portion of the needle 14, the flared portion is swaged so that the needle 14 securely surrounds and attaches to the band 12.

Figure 6E:
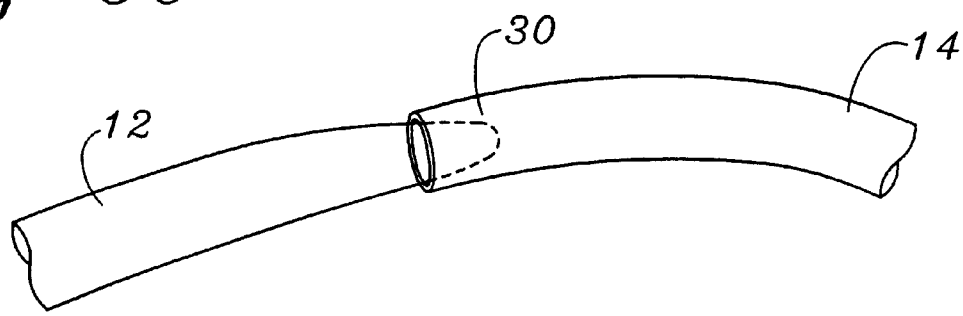

In each of the previously described embodiments of attaching the band 12 to the needle 14, the distal end 30 of the needle 14 has a larger diameter than the proximal end 34 of the band 12 in order to allow the band 12 to be inserted into the hollow portion of the needle 14. Alternatively, using a modified extrusion or molding process, the band 12 includes a smaller stepped-diameter portion at its proximal end 34. In this embodiment, shown in FIG. 6e, the diameter of the distal end 30 of the needle 14 is similar to the diameter along the length of the band 12, excluding its tapered portion. This embodiment of the present invention provides for a more continuous diameter along the length of the band 12 and the needle 14 which may facilitate adjustment of the device during implantation.

Figure 6F:
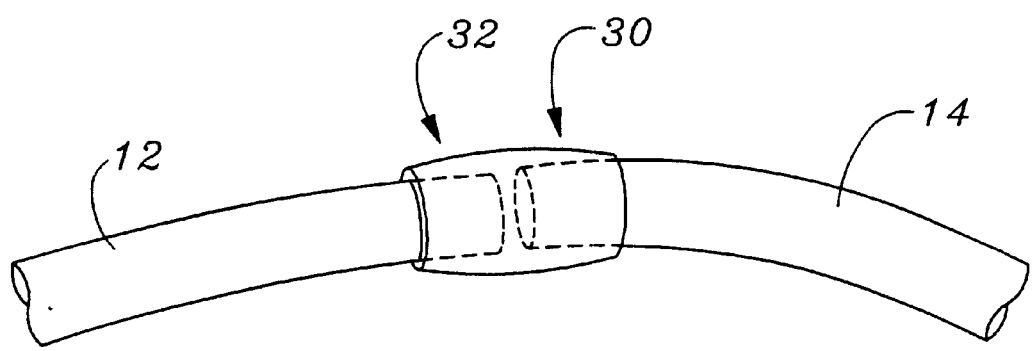

In a further embodiment, a sleeve is used to connect the end 32 of the band 12 to the end 30 of the needle 14, as shown in FIG. 6f. After the sleeve is positioned over the proximal end 32 of the band 12 and the distal end 30 of the needle 14, the sleeve is crimped and/or swaged down thereby mechanically attaching the band 12 and needle 14.

In another embodiment of the present invention, the proximal end 32 of the band 12 is hollowed-out and the distal end 30 of the needle 14 is inserted and attached to the band 12. The various means of attachment can be the same as those previously described embodiments wherein the distal end 30 of the needle 14 is hollowed-out and the proximal end 32 of the band 12 is inserted and attached to the needle 14.

After the band 12 is implanted in the AV groove, a fit adjuster 16 is used to size and position the band 12 in the annulus. The fit adjuster 16 is securely attached to the distal end 36 of the band 12 using mechanical or chemical means similar to those previously described for the band 12 and needle 14. Any polymer or alloy that can be molded or machined and is approved for tissue contact can be used to manufacture the fit adjuster 16. Preferably, the material can also be sterilized using conventional sterilization methods, such as gamma radiation, steam, ethylene oxide (EtO) and the like. In a preferred embodiment, the fit adjuster 16 is made of polysulfone and is sterilized using radiation.

Figure 7A:
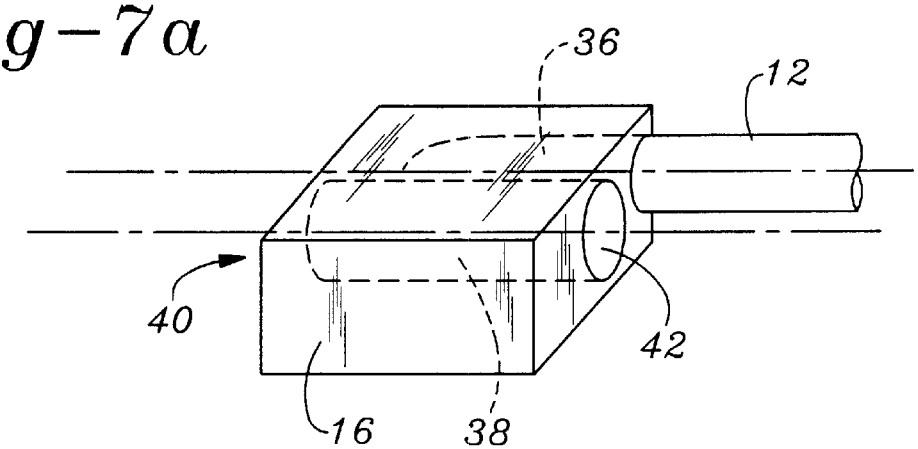
FIGS. 7a–7e are cross-sectional perspective views of various embodiments of a fit adjuster in accordance with a preferred embodiment of the present invention.

As shown in FIGS. 6a and 7a, the fit adjuster 16 is cube-shaped and includes a through-hole or conduit 38 that runs parallel to the axis of the through- or blind-hole (not shown) that contains the proximal end 36 of the band 12. In this embodiment, the through-hole 38 and the proximal end 36 of the band 12 are separate from each other. The through-hole 38 includes an entrance port 40 located on a first side of the fit adjuster 16 and an exit port 42 located on the second side that is opposite to the first side of the fit adjuster 16. The diameter of the through-hole 38 should be configured to allow the needle 14 and a portion of the band 12 to pass therethrough. However, the through-hole 38 of the fit adjuster 16 should provide sufficient friction with the band to prevent the needle 14 and/or band 12 from slipping out of the through-hole 38 during the procedure.

Figure 7B:
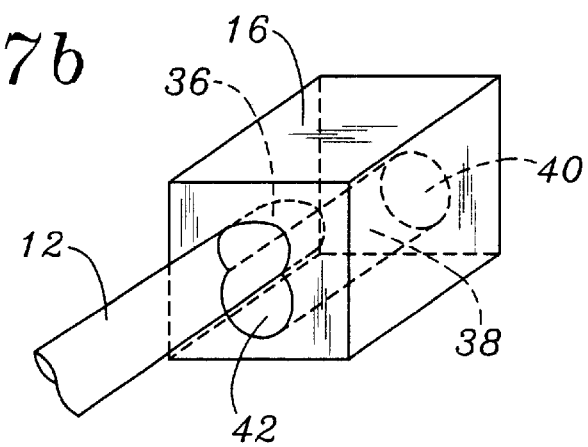

In another embodiment, a portion of the through-hole 38 and the proximal end 36 of the band 12 intersect, as shown in FIG. 7b. The section of the band 12 that intersects the area of the through-hole 38 produces an interference fit when the needle 14 and attached portion of the band 12 are inserted through the hole 38. The interference fit prevents the needle 14 and band 12 from slipping out of the fit adjuster 16 during the procedure.

Figure 7C:
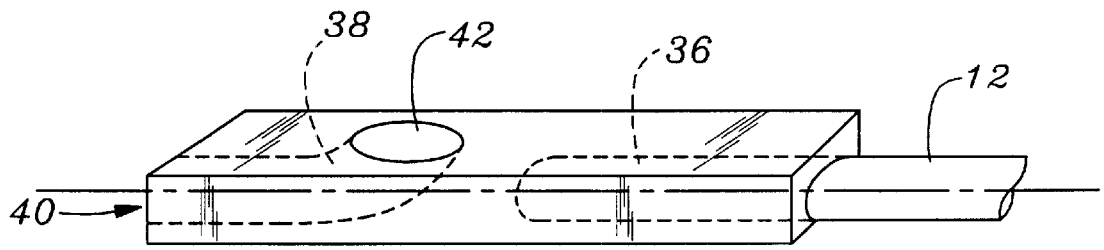
Figure 7D:
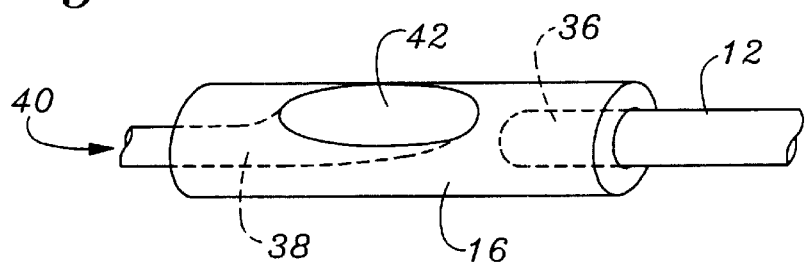

In another embodiment, as shown in FIG. 7c, the fit adjuster 16 is in the shape of a six-sided polyhedron. The proximal end 32 of the band 12 and the through-hole 38 approximately share the same axis. However, the entrance port 40 and exit port 42 of the through-hole 38 are located on adjacent sides of the fit adjuster 16. The through-hole 38 is curved to allow passage of the needle 14. Therefore, the band 12 must bend slightly in order to emerge from the exit port 42. In addition, the shape of the exit port 42 includes a narrowed portion which provides increased friction between the band 12 and fit adjuster 16 during the sizing procedure. Alternatively, as shown in FIG. 7d, the fit adjuster 16 may be cylindrically shaped.

Figure 7E:
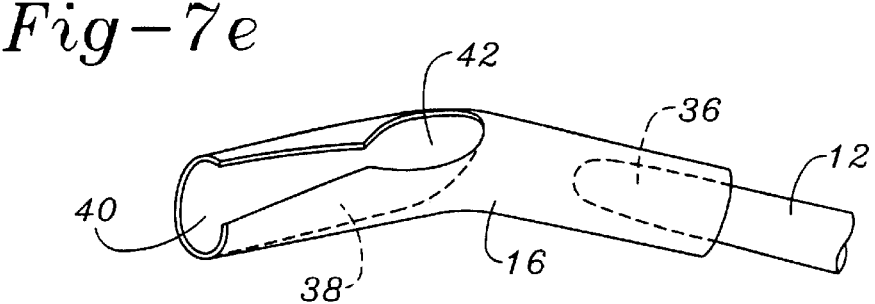

FIG. 7e shows another embodiment of the fit adjuster 16 of the present invention. In this embodiment, the fit adjuster 16 is cylindrically shaped, similar to the embodiment disclosed in FIG. 7d. However, there is a slight bend near the central area of the fit adjuster 16. Since the entrance and exit ports 40, 42 are located on the same bent portion of the fit adjuster 16, the passageway or conduit formed between the entrance port 40 and exit port 42 is relatively linear. By forming a slight bend in the fit adjuster 16, the band 12 can emerge from the exit port 42 with an improved exit angle for adjustment of the band 12.

Other shapes and configurations of the fit adjuster 16 can also be used in accordance with the present invention, provided that the band 12 can be attached to the fit adjuster 16 and that the fit adjuster includes the ability to position the band 12 and adjust its tension by cinching the band 12 while the device maintains adequate force on the valve annulus to effect the repair until surgical attachment devices are put in place. Various mechanical means not disclosed but well known in the art may also be employed to temporarily and/or permanently secure the needle 14 or band 12 to the fit adjuster 16 during the annuloplasty procedure.

Method of Implantation

The present invention also contemplates a method of implanting the annuloplasty system 10 into the AV groove of a patient, as shown in FIGS. 8–11. The first step of implanting the annuloplasty system 10 into the AV groove includes inserting the tapered end of the needle 14 through the endocardium adjacent to the trigone or commissure 44 of the valve annulus 46. The needle 14 can be inserted into either the right or left trigone 44, depending on surgeon preference. As the needle 14 is maneuvered through the fatty tissue along the AV groove in the annulus 46, it pulls the band 12 behind it.

Figure 8:
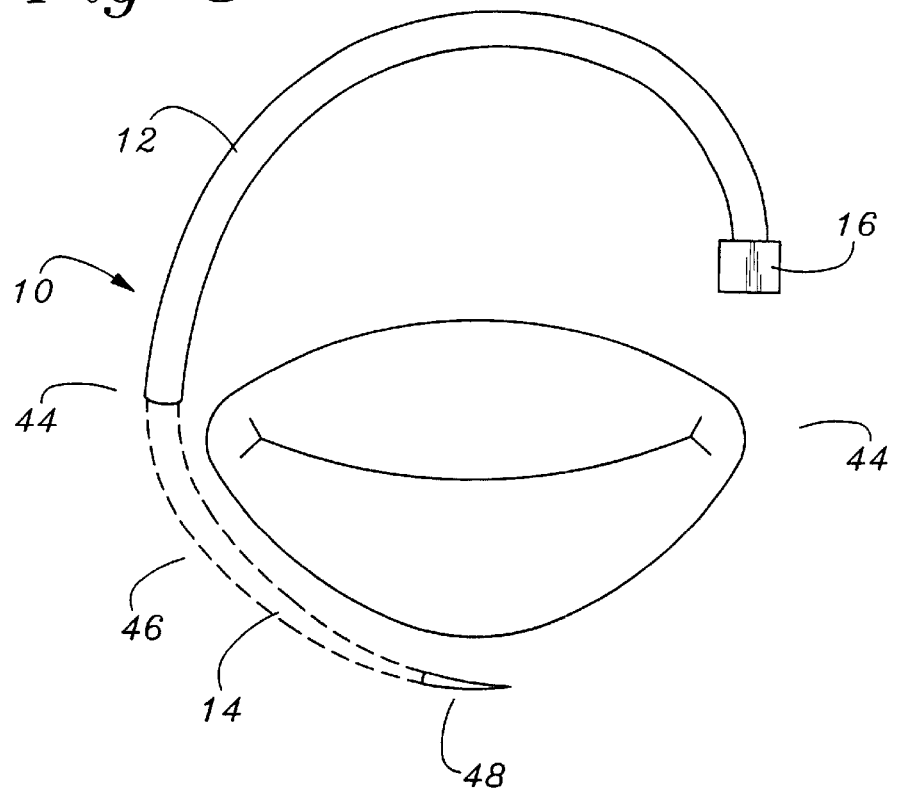
FIG. 8 is a plan view of a valve illustrating implantation of the annuloplasty system in accordance with a preferred embodiment of the present invention.
Figure 9:
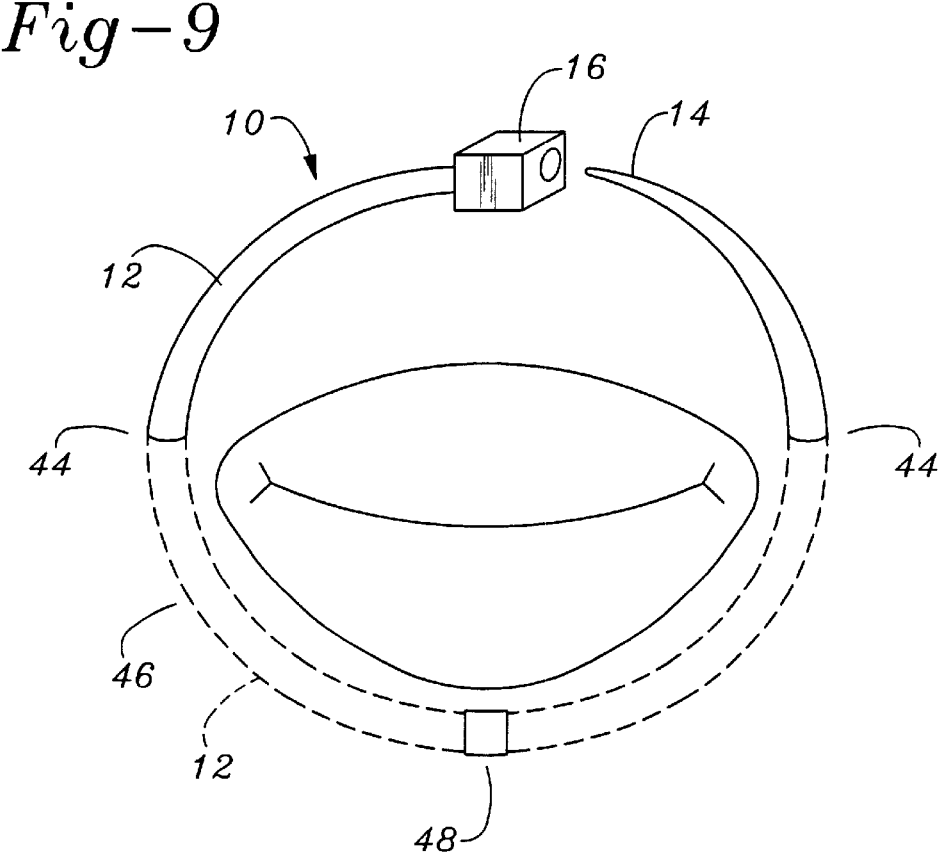
FIG. 9 is a plan view of a valve illustrating implantation of a band in accordance with a preferred embodiment of the present invention.

The next steps involve exiting and reentering the AV groove near the mid-point 48 of the annulus 46, as shown in FIGS. 8 and 9. Due to the geometry of the valve and annuloplasty system 10 and the limited amount of working space available to the surgeon in the area of the valve, the needle 14 will most likely have to exit and reenter the AV groove, although it is possible that the implant process could be performed in one bite in a smaller annulus. Forceps can be used to carefully pull the needle 14 out of the tissue in the midpoint 48 area and then reinsert the needle 14 into the tissue. A minimal amount of space should exist between the exit and reentrance points of the needle 14 in the midpoint 48 section of the AV groove, as shown in FIG. 9. Ideally, the entrance and exit points share the same perforation of the endocardium. This maximizes band 12 retention by the tissue and minimizes the amount of material exposed to blood flow. After the needle 14 is reinserted into the AV groove near the midpoint 48 of the annulus 40, it is manipulated through the tissue until it reaches the other trigone 44 of the valve.

Figure 10:
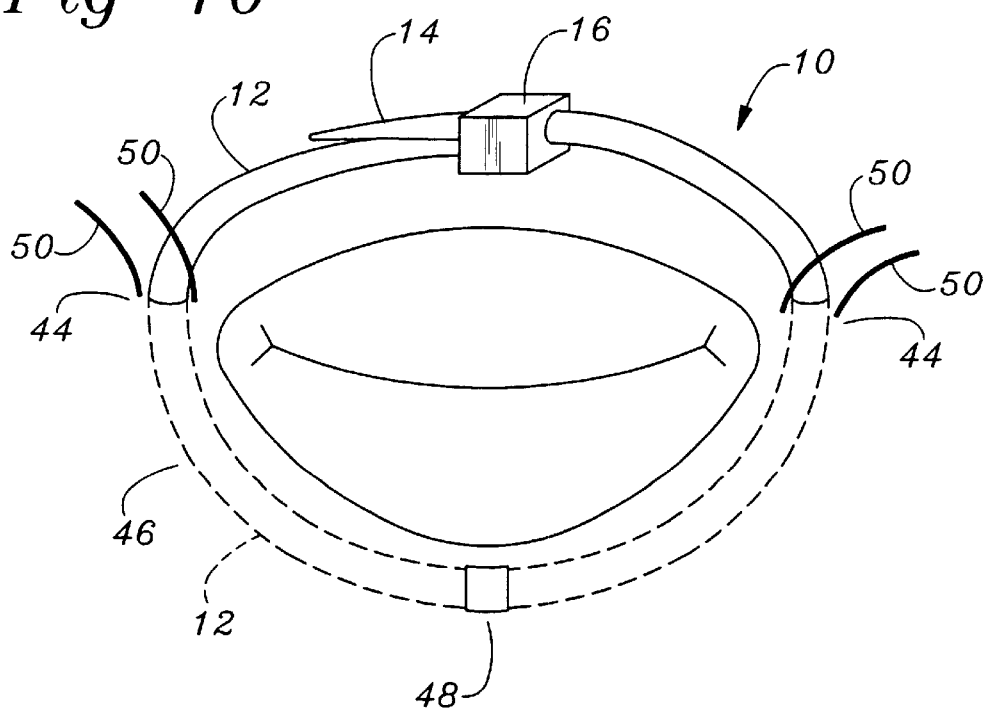
FIG. 10 is a plan view of a valve illustrating the method of sizing an annuloplasty system in accordance with a preferred embodiment of the present invention.

The subsequent steps include directing the needle 14 through the endocardium adjacent to the other trigone 44 of the valve and sizing the annuloplasty system 10. Using forceps or a similar device, the tapered end of the needle 14 is directed through the tissue adjacent to the location of the other trigone 44, as shown in FIG. 9. The needle 14 is pulled out of the tissue until a portion of the band 12 is exposed. As shown in FIG. 10, the proximal end 34 of the needle 14 is then inserted into the through-hole 44 of the fit adjuster 16. Using the fit adjuster 14, the band 12 is positioned and sized, by pulling it through the through-hole 44 and cinching the tissue, in the AV groove until the valve annulus 46 is reconfigured to an optimal shape.

The final assembly steps include securing the band 12 to the valve annulus 46 and removing the exposed portion of the annuloplasty system 10. Once the band 12 is appropriately sized and positioned in the AV groove, the band 12 is secured to the tissue so that the valve annulus 46 will retain its shape. At least one suture 50 placed into each of the trigones 44 is used to fasten the band 12 to the tissue. Although a suture 50 is a preferred attachment device, surgical staples, clamps, cyanoacrylate and other surgical attachment devices may also be used. The suture 50 penetrates through the tissue and the overwrap layer 24 (FIGS. 3a–3c) or tubular textile 28 (FIG. 5) of the band 12 to ensure proper attachment. The suture penetrates the overwrap layer 24 (FIGS. 3a–3c) or tubular textile 28 (FIG. 5) of the band 12 to prevent the suture from possibly tearing out of the band 12 and the tissue of the annulus.

However, based upon the material characteristics of the band 12, the surgical attachment device may simply surround a portion of the band 12. Therefore, due to the structural integrity of the band 12, the attachment device surrounds the band 12 in a manner to adequately secure the band 12 to the tissue without penetrating the band 12.

Figure 11:
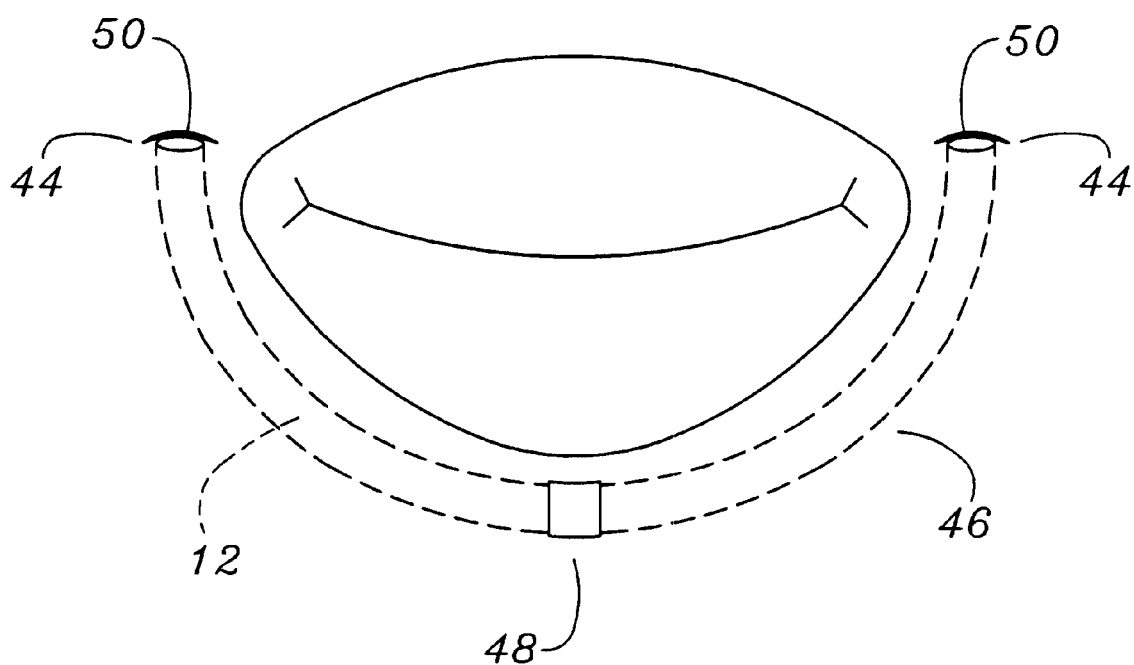
FIG. 11 is a plan view of a valve after completion of an annuldplasty procedure in accordance with a preferred embodiment of the present invention.

After the band 12 is sutured to the tissue at both of the trigones 44, the remaining or exposed portion of the annuloplasty system 10 is removed, as shown in FIG. 11. At this point, the trigonal attachment sutures may be used to close the endocardium over the band at the entrance and exit locations adjacent to the trigones minimizing blood exposure. Optimally, an additional suture or other surgical attachment device may be placed at the mid-posterior annulus entrance-exit location to close the endocardium. Prior to removing the remaining portion of the annuloplasty system 10, a retaining suture may be affixed to the fit adjuster 16 to minimize the risk of this small component falling into the ventricle undetected during the implant procedure. Alternatively, such a retaining suture may be provided to the surgeon pre-attached to the fit adjuster 16 by the manufacturer. Since the majority of the band 12 is embedded within the tissue, only a small amount of material is exposed to blood flow, thereby greatly minimizing the risk of thrombosis.

As another method, the sutures may be placed into the trigones prior to implantation of the band 12 in the annulus. This method facilitates identification of the location of the trigones for easier and more accurate insertion of the needle 14 in the adjacent area. In addition, since the sutures are in place prior to implantation of the band 12, there is less trauma and manipulation to the band 12 entrance and exit points in the area adjacent to the trigones when the band 12 is secured to the tissue.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of implanting an annuloplasty system in a patient's heart comprising the steps of:

providing an annuloplasty band having at least one fiber along its length and a needle attached to one end of said band;

inserting said needle adjacent to a first trigone of a valve annulus;

maneuvering said needle and said band through tissue of an arterioventricular groove of said annulus;

directing said needle and said band to exit said tissue at a first point located in a region near a midpoint area of said arterioventricular groove and reinserting said needle and said band into said tissue at a second point located near said first point of said arterioventricular groove;

directing said needle to again exit said tissue at a second trigone of said valve annulus; and securing said band to said valve annulus using a surgical attachment device.

2. The method of claim 1, wherein said surgical attachment device is a suture.

3. The method of claim 2, wherein said suture penetrates through said band.

4. The method of claim 1, further comprising the step of sizing said annuloplasty system using a fit adjuster.

5. The method of claim 4, wherein said sizing step further includes inserting said needle and a portion of said band into a through-hole of said fit adjuster.

6. The method of claim 5, wherein said sizing step further includes using said fit adjuster to position and size said band in said arterioventricular groove until said valve annulus is reconfigured to an optimal shape.

7. The method of claim 4, wherein a retaining suture is affixed to said fit adjuster to minimize the risk of said fit adjuster falling into a ventricle of said heart.

8. The method of claim 1, further comprising the step of removing an exposed portion of said annuloplasty system to minimize material exposure to blood flow.

9. The method of claim 1, wherein said at least one fiber of said band includes a plurality of fibers interlaced along a length of said band.

10. The method of claim 9, wherein said step of securing said band includes penetrating said suture into said plurality of fibers interlaced along a length of said band.

11. The method of claim 9, wherein said plurality of fibers interlaced along a length of said band are sized to ensure that said suture will catch on said fibers and prevent said suture from tearing out of said band during installation.

12. The method of claim 9, wherein said plurality of fibers is a tubular textile.

13. The method of claim 12, wherein said securing step includes using a suture that penetrates through a tubular textile of said band.

14. The method of claim 1, wherein said step of reinserting is performed so as to minimize distance between said first point and said second point.

15. The method of claim 1, further comprising the step of suturing a portion of endocardium to close all entrance and exit sites to minimize blood exposure.

16. The method of claim 1, wherein said step of reinserting is performed so that said needle passes through the same perforation point of the endocardium.

17. The method of claim 1, wherein said at least one fiber of said band is a reinforcing filament located in a region near a central core of said band.

18. The method of claim 17, wherein said band has four fibers.

19. The method of claim 1, wherein said at least one fiber is non-distensible.

20. The method of claim 1, wherein said band is secured to said tissue so that said valve annulus will retain its shape.

21. A method of implanting an annuloplasty system in a patient's heart comprising the steps of:

providing an annuloplasty band having a central core and at least one fiber located in a region near the central core and extending linearly along its length and a needle attached to one end of said band;

inserting said needle adjacent to a first trigone of a valve annulus;

maneuvering said needle and said band through tissue of an arterioventricular groove of said annulus;

directing said needle to exit said tissue at a second trigone of said valve annulus; and securing said band to said valve annulus using a surgical attachment device, wherein said central core of said band is formed of a generally cylindrical silicone element, and furthers including a plurality of fibers interlaced around the exterior of the central core, wherein the surgical attachment device is a suture and the method includes threading the suture through the annuloplasty band so that said suture will catch on said interlaced fibers.

22. The method of claim 21, wherein said at least one fiber is a suture.

23. The method of claim 21, wherein said at least one fiber of said band includes a plurality of fibers extending linearly along a length of said band.

24. The method of claim 21, further including facilitating passage of the band through the tissue of the arterioventricular groove by providing an overcoat layer of a lubricious material surrounding the plurality of fibers around the exterior of the central core.

25. A method of implanting an annuloplasty system in a patient's heart comprising the steps of:

providing an elongate annuloplasty band having a first end a second end with a needle attached to the second end;

inserting said needle adjacent to a first trigone of a valve annulus;

maneuvering said needle and said band through tissue of an arterioventricular groove of said annulus;

directing said needle to exit said tissue at a second trigone of said valve annulus such that the first and second ends of the band are exposed;

securing said fist and second ends of the band to the respective first and second trigones; and removing the exposed portion of said annuloplasty band between the first and second trigones.

26. The method of claim 25, further comprising:

directing said needle and said band to exit said tissue at a first point located in a region near a midpoint area of said arterioventricular groove and reinserting said needle and said band into said tissue at a second point located near said first point of said artenoventricular groove.

27. The method of claim 26, wherein said step of reinserting is performed so that said needle passes through a same perforation point of the tissue.

28. The method of claim 27, further comprising the step of suturing the tissue at all insertion and exit sites to minimize blood exposure.

29. The method of claim 25, further comprising the step of suturing the tissue both at the insertion and exit sites to minimize blood exposure.

30. The method of claim 25, further comprising the step of sizing said annuloplasty system using a fit adjuster, the method including engaging the fit adjuster with both the first and second ends of the band.

31. The method of claim 30, wherein a retaining suture is affixed to said fit adjuster to minimize the risk of said fit adjuster falling into a ventricle of said heart in the step of removing the exposed potion of said annuloplasty-band.

* * * * *